United States Patent
Lin et al.

(10) Patent No.: US 11,010,893 B2
(45) Date of Patent: May 18, 2021

(54) IMAGE IDENTIFYING METHOD AND IMAGE IDENTIFYING DEVICE

(71) Applicant: Wistron Corporation, New Taipei (TW)

(72) Inventors: Zhe-Yu Lin, New Taipei (TW);
Zhao-Yuan Lin, New Taipei (TW);
Yu-Jie Huang, New Taipei (TW);
Yi-Sheng Chao, New Taipei (TW);
Chun-Peng Hsu, New Taipei (TW)

(73) Assignee: Wistron Corporation, New Taipei (TW)

( * ) Notice: Subject to any disclaimer, the term of this patent is extended or adjusted under 35 U.S.C. 154(b) by 79 days.

(21) Appl. No.: 16/443,787

(22) Filed: Jun. 17, 2019

(65) Prior Publication Data

US 2020/0302597 A1    Sep. 24, 2020

(30) Foreign Application Priority Data

Mar. 19, 2019   (TW) .................................. 108109259

(51) Int. Cl.
*G06T 7/00*     (2017.01)
*A61B 6/03*     (2006.01)
*A61B 6/00*     (2006.01)

(52) U.S. Cl.
CPC ............ *G06T 7/0012* (2013.01); *A61B 6/032* (2013.01); *A61B 6/5205* (2013.01); *G06T 2207/30056* (2013.01)

(58) Field of Classification Search
CPC .................. G06T 2207/10072; A61B 17/1703
(Continued)

(56) References Cited

U.S. PATENT DOCUMENTS

2006/0013460 A1    1/2006 Dehmeshki
2016/0148375 A1*   5/2016 Oh .......................... G16H 30/20
                                                  382/131
(Continued)

FOREIGN PATENT DOCUMENTS

CN    109102506    12/2018
TW    200602006     1/2006

OTHER PUBLICATIONS

"Office Action of Taiwan Counterpart Application", dated Mar. 26, 2020, p. 1-p. 8.
(Continued)

*Primary Examiner* — Kiet M Doan
(74) *Attorney, Agent, or Firm* — JCIPRNET (57) ABSTRACT

The disclosure provides an image identifying method and an image identifying device. The method includes: retrieving a first computer tomographic (CT) image including a plurality of first pixels; retrieving a plurality of second pixels from the first pixels, and generating a second CT image based on the second pixels; performing a contrast enhancement algorithm on the second CT image to adjust a contrast of the second CT image; identifying a first image region in the second CT image to generate a third CT image, wherein the first image region includes a first object; dividing the third CT image into a plurality of sub-images, and only reserving a specific image region corresponding to the first object in each sub-image; combining the sub-images into a fourth CT image; and identifying an object type of the first object based on the fourth CT image.

18 Claims, 4 Drawing Sheets

(58) Field of Classification Search
USPC .................................... 382/131; 378/98.12
See application file for complete search history.

(56) References Cited

U.S. PATENT DOCUMENTS

2019/0005644 A1* 1/2019 Yaguchi ................ G16H 30/40
2019/0344493 A1* 11/2019 Amano ................ B29C 64/393

OTHER PUBLICATIONS

"Search Report of Europe Counterpart Application", dated Nov. 6, 2019, pp. 1-8.

* cited by examiner

IMAGE IDENTIFYING METHOD AND IMAGE IDENTIFYING DEVICE

CROSS-REFERENCE TO RELATED APPLICATION

This application claims the priority benefit of Taiwan application serial no. 108109259, filed on Mar. 19, 2019. The entirety of the above-mentioned patent application is hereby incorporated by reference herein and made a part of this specification.

BACKGROUND

Technical Field

The disclosure relates to an identifying method and an identifying device, and particularly relates to an image identifying method and an image identifying device.

Description of Related Art

In recent years, the number of patients suffering from liver diseases keeps increasing. In general, after computed tomography (CT) images of the patients are captured, the radiologist takes over to give a diagnosis on the disease. However, due to limited medical human resources and other related resources, the diagnosing processes may be time-consuming. Besides, some diseases need to be diagnosed by a more experienced radiologist. Therefore, given the current number of radiologists, it may be difficult to cope with the increasing number of patients with liver diseases.

Currently, while there are many systems for detecting tumor locations, most of these systems are provided to detect nodules in the chest, and no product for detecting tumors in the liver or the abdominal cavity is available on the market. Even though a certain number of studies have devoted efforts in liver tumor detection, these studies only focus on detection of hepatocellular carcinoma (HCC), and the accuracy thereof is yet to meet the standard for commercialization. Moreover, there are as many as tens of types of liver diseases, so simply detecting one of the diseases is clearly not enough for application in actual cases.

SUMMARY

Accordingly, the disclosure provides an image identifying method and an image identifying device for addressing the above technical issues.

An embodiment of the disclosure provides an image identifying method. The image identifying method includes: retrieving a first computer tomographic (CT) image, wherein the first CT image includes a plurality of first pixels, each of the first pixels has a channel value, and the channel value of each of the first pixels falls within a first range; retrieving a plurality of second pixels from the first pixels, and generating a second CT image based on the second pixels, wherein the channel value of each of the second pixels falls within a second range, and the second range is smaller than the first range; performing a contrast enhancement algorithm on the second CT image, so as to adjust a contrast of the second CT image; identifying a first image region in the second CT image to generate a third CT image, wherein the first image region includes a first object; dividing the third CT image into a plurality of sub-images, and only reserving a specific image region corresponding to the first object in each sub-image; combining the sub-images into a fourth CT image; and identifying an object type of the first object based on the fourth CT image.

An embodiment of the disclosure provides an image identifying device. The image identifying device includes a storage circuit and a processor. The storage circuit stores a plurality of modules. The processor is coupled to the storage circuit and accesses the modules to perform the following: retrieving a first computer tomographic (CT) image, wherein the first CT image includes a plurality of first pixels, each of the first pixels has a channel value, and the channel value of each of the first pixels falls within a first range; retrieving a plurality of second pixels from the first pixels, and generating a second CT image based on the second pixels, wherein the channel value of each of the second pixels falls within a second range, and the second range is smaller than the first range; performing a contrast enhancement algorithm on the second CT image, so as to adjust a contrast of the second CT image; identifying a first image region in the second CT image to generate a third CT image, wherein the first image region includes a first object; dividing the third CT image into a plurality of sub-images, and only reserving a specific image region corresponding to the first object in each sub-image; combining the sub-images into a fourth CT image; and identifying an object type of the first object based on the fourth CT image.

Based on the above, the image identifying method and the image identifying device according to the embodiments of the disclosure are capable of sequentially performing identification to find the first image region, the specific image region corresponding to the first object, and the object type of the first object after excluding the pixels whose channel values do not fall within the first range and performing the contrast enhancement algorithm. Accordingly, the performance and accuracy of identification can be more favorable.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Reference will now be made in detail to the present preferred embodiments of the disclosure, examples of which are illustrated in the accompanying drawings. Wherever possible, the same reference numbers are used in the drawings and the description to refer to the same or like parts.

In brief, an image identifying device according to the embodiments of the disclosure is capable of performing identification on a specific computer tomographic (CT)

image to find a specific object in the specific image and further identifying an object type of the specific object after retrieving the specific CT image. In an embodiment, the image identifying device of the disclosure is capable of performing identification on a CT image to find a tumor in the CT image and further determining a tumor type of the tumor after retrieving the CT image. For the ease of description, it is assumed in the following that the target on which the image identifying device performs the image identification is an abdominal CT image captured from a patient, and relevant identifying operations performed by the image identifying device based on the abdominal CT image will be described in detail in the following.

Figure 1:
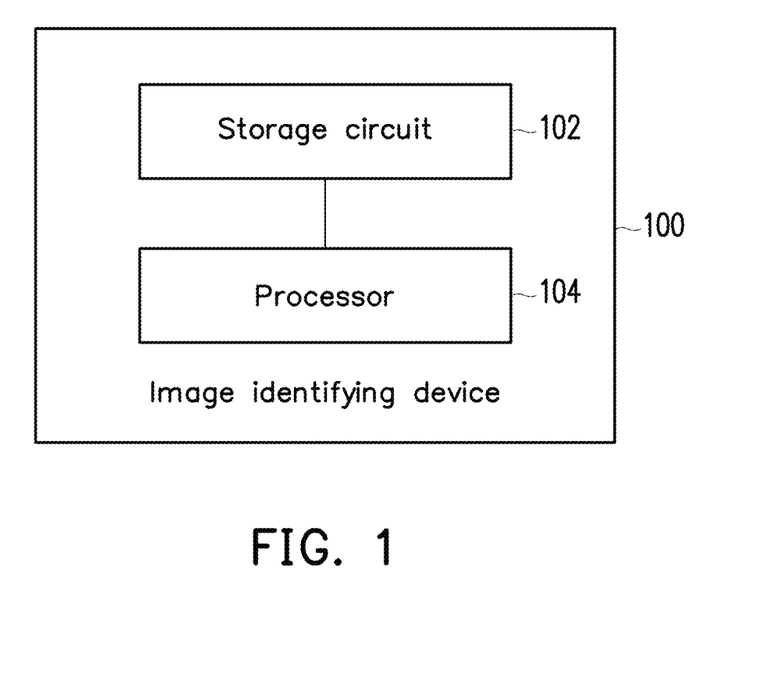
FIG. 1 is a schematic view illustrating an image identifying device according to an embodiment of the disclosure.

Referring to FIG. 1, FIG. 1 is a schematic view illustrating an image identifying device according to an embodiment of the disclosure. In FIG. 1, an image identifying device 100 includes a storage circuit 102 and a processor 104. In different embodiments, the image identifying device 100 may be a personal computer, a laptop computer, a workstation, a sever, a smart device, or other devices capable of analyzing and processing a CT image. However, the disclosure is not limited thereto.

The storage circuit 102 may be, for example, any type of fixed or movable random access memories (RAMs), read-only memories (ROMs), flash memories, hard drives, other similar devices, or a combination of these devices, and the storage circuit 102 may serve to record a plurality of program codes or modules.

The processor 104 is coupled to the storage circuit 102, and may be a general-purpose processor, a specific-purpose processor, a traditional processor, a digital signal processor, a plurality of microprocessors, one or more microprocessors incorporating a digital signal processor core, a controller, a microcontroller, an application specific integrated circuit (ASIC), a field programmable gate array (FPGA), any other type of integrated circuits, state machines, advanced RISC machine (ARM)-based processors, or similar products.

In the embodiments of the disclosure, the processor 104 may access the modules and program codes recorded in the storage circuit 102 to realize the image identifying method of the disclosure. Details in this regard will be described in the following.

Figure 2:
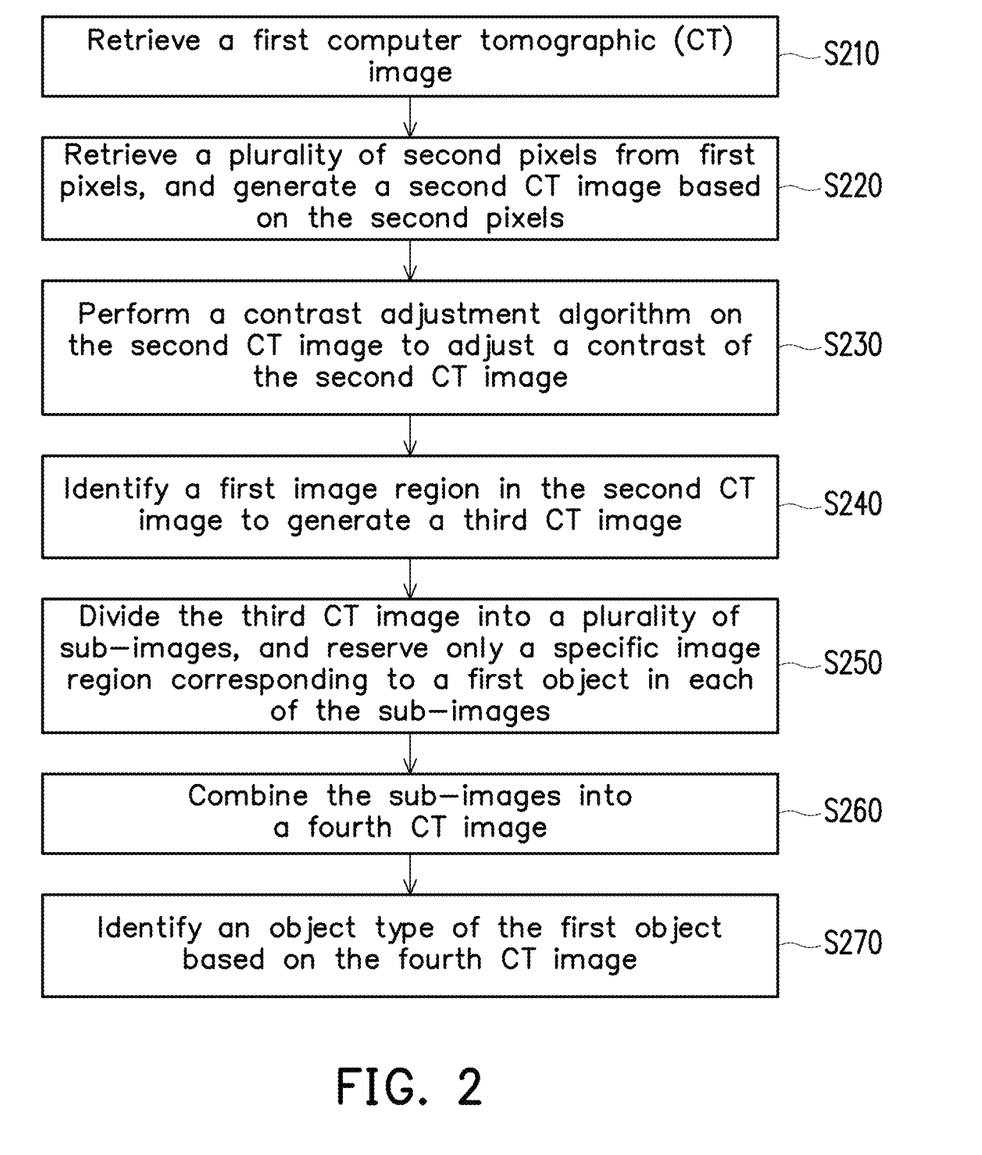
FIG. 2 is a flowchart illustrating an image identifying method according to an embodiment of the disclosure.

Referring to FIG. 2, FIG. 2 is a flowchart illustrating an image identifying method according to an embodiment of the disclosure. The method of the embodiment may be carried out by the image identifying device 100 of FIG. 1. In the following, details of the respective steps shown in FIG. 2 are described with reference to the components shown in FIG. 1. Besides, to more clearly describe the concept of FIG. 2, the description is also made with reference to the scenario shown in FIG. 3. However, it should be noted that FIG. 3 merely serves as an example and shall not be construed as a limitation on possible embodiments of the disclosure.

Figure 3:
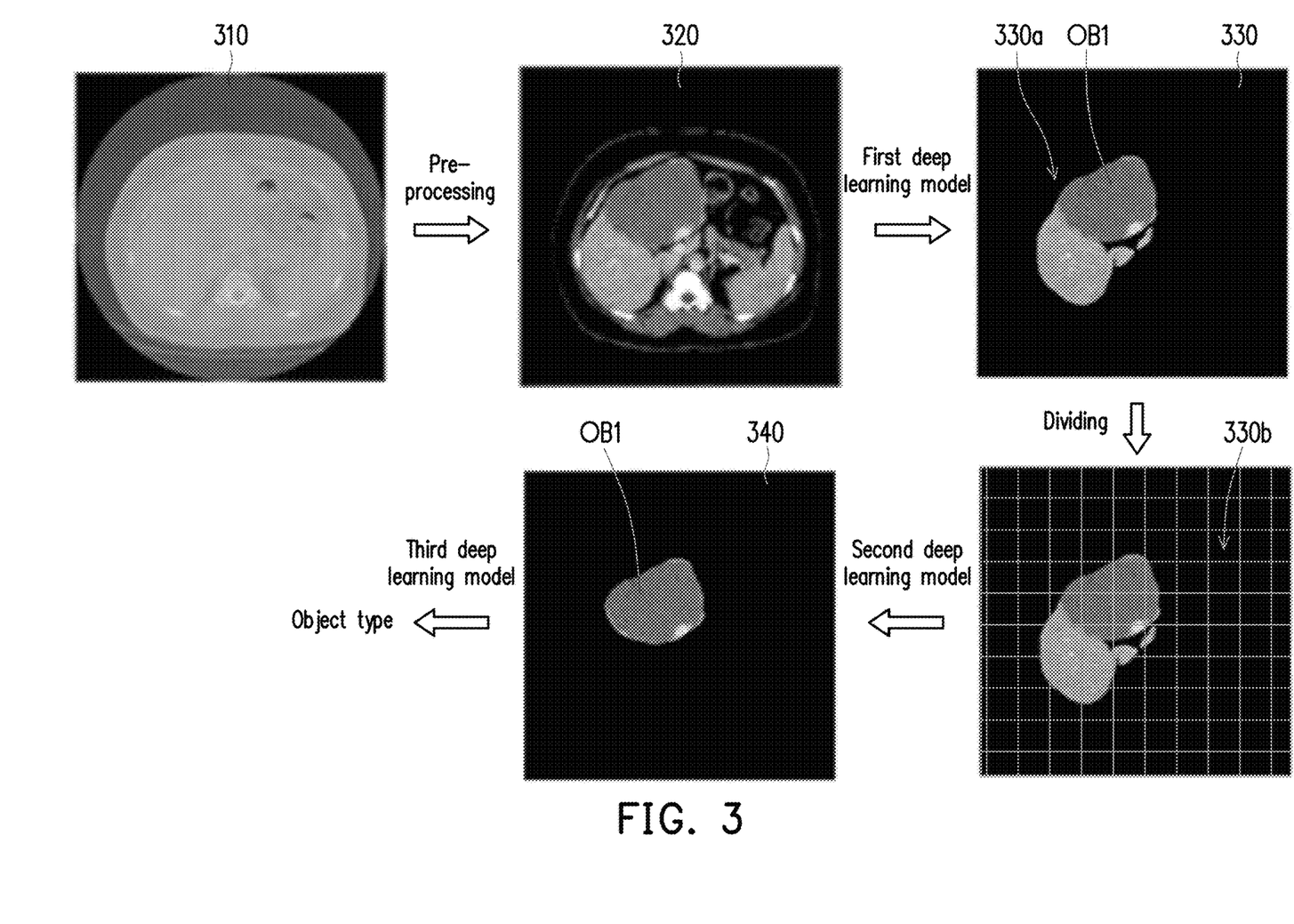
FIG. 3 is a view illustrating a usage scenario according to an embodiment of the disclosure.

First of all, in Step S210, the processor 104 may retrieve a first CT image 310. In the embodiment, the first CT image 310 is, for example, an abdominal CT image captured from the abdominal cavity of a patient. In addition, the image identifying device 100 according to the embodiment of the disclosure may, after performing specific pre-processing on the first CT image 310, find the liver, a tumor in the liver, and a tumor type of the tumor in a pre-processed image by using different deep-learning models. However, the disclosure is not limited thereto.

The first CT image 310 may include a plurality of first pixels. In addition, based on the properties of a normal CT image, each of the first pixels has a channel value, and the channel value falls within a first range. In the embodiment, the channel value is, for example, a Hounsfield unit (HU) value, and an HU value normally falls between −2048 and 30000 (i.e., the first range). However, the disclosure is not limited thereto.

However, the first range of the HU value is too broad for the processor 104 to perform a subsequent relevant identification process. Therefore, the processor 104 may exclude some of the first pixels through Step S220, so as to improve the performance of the subsequent identification process.

In Step S220, the processor 104 may retrieve a plurality of second pixels from the first pixels, and generate a second CT image based on the second pixels. The channel value of each of the second pixels falls within a second range, and the second range is smaller than the first range. In an embodiment, the processor 104 may find a plurality of third pixels from the first pixels, and the channel value of each of the third pixels falls outside the second range. In addition, the processor 104 removes the third pixels from the first CT image to generate the second CT image 320 only including the second pixels. In short, after defining the smaller second range, the processor 104 may remove the third pixels whose channel values do not fall within the second range in the first CT image 310, so that only the second pixels whose channel values fall within the second range are retained in the first CT image, thereby forming the second CT image 320.

In different embodiments, the second range may be set by the designer based on needs. In an embodiment, since the HU value corresponding to a liver and a tumor normally falls between −70 and 200, the processor 104 may define the second range as ranging between −70 and 200. However, the disclosure is not limited thereto. In other embodiments, the processor 104 may also be configured to generate other second CT images based on one or more other second ranges. In other words, each of these other second CT images may only include pixels whose channel values fall within a specific range. In an embodiment, the other one or more second ranges may be determined according to a HU value which makes the liver and a tumor more identifiable after the practical modifications and testing of a radiologist. However, the disclosure is not limited thereto.

Then, in Step S230, the processor 104 may perform a contrast enhancement algorithm on the second CT image 320, so as to adjust the contrast of the second CT image 320. In an embodiment, the contrast enhancement algorithm may include a histogram equalization algorithm or other similar algorithms, for example. However, the disclosure is not limited thereto. Specifically, after the contrast enhancement algorithm is performed on the second CT image 320, the contrast between image regions corresponding to the liver and the tumor may be increased, so that the tumor becomes more identifiable. However, the disclosure is not limited thereto.

According to the above, in the embodiments of the disclosure, the performance of the image identification (e.g., tumor identification) performed subsequently is facilitated through pre-processing such as removing the pixels whose channel values do not fall within the first range and performing the contrast enhancement algorithm.

Then, in Step S240, the processor 104 may identify a first image region 330a in the second CT image 320, so as to generate a third CT image 330. In FIG. 3, the first image region 330a may be, for example, an image region of the liver including a tumor, and the first image region 330a may include a first object OB1. In the embodiment, the first object OB1 is, for example, a tumor located in the liver. However, the disclosure is not limited thereto. In an embodiment, the processor 104 may input the second CT image 320 to a first deep learning model to find the first image region 330a in the second CT image 320 according to the first deep learning model. Then, the processor 104 may remove the second pixels not belonging to the first image region 330a from the second CT image 320, so as to generate the third CT image 330.

In an embodiment, the first deep learning model may be realized by adopting the Unet model under the framework of the convolutional neural network (CNN) or other similar models. However, the disclosure is not limited thereto. Besides, before being used to find the first image region 330a, the first deep learning model may be firstly trained with training images in which specific regions of interest (ROIs) are labeled, so as to learn the features of the ROIs through the training images. Therefore, in the embodiment, in order for the first deep learning model to be capable of identifying the first image region 330a (i.e., the image region of the liver having the tumor), the first deep learning model may firstly learn based on a plurality of training images which are images of livers having tumors as the ROIs, so as to find the features of the image region of the liver having a tumor.

Then, in Step S250, the processor 104 may divide the third CT image 330 into a plurality of sub-images 330b, and reserve only a specific image region corresponding to the first object OB1 in each of the sub-images 330b. In an embodiment, the processor 104 may input a first sub-image of the sub-images into a second deep learning model, so as to find the specific image region corresponding to the first object OB1 in the first sub-image based on the second deep learning model. In addition, each of the sub-images includes a plurality of specific pixels. Then, the processor 104 may remove the specific pixels not belonging to the specific image region from the first sub-image, so that the first sub-image only includes the specific image region corresponding to the first object OB1.

In an embodiment, the processor 104 may evenly divide the third CT image 330 into the sub-images 330b according to a predetermined size. For example, assuming that the size of the third CT image 330 is 512×512 and the predetermined size is 64×64, the processor 104 may evenly divide the third CT image 330 into 64 sub-images 330b according to the predetermined size. The size of each of the sub-images 330b is the predetermined size (i.e., 64×64). However, the disclosure is not limited thereto. In addition, the processor 104 may further record the distributed locations of the sub-images 330b in the third CT image 330. For example, the distributed location of each of the sub-images 330b may be represented as coordinates of each of the sub-images 330b in the third CT image 330. However, the disclosure is not limited thereto.

Then, the processor 104 may input the respective 64 sub-images 330b to the second deep learning model, so as to find the specific image region corresponding to the first object OB1 in each of the sub-images 330b according to the second deep learning model. Then, the processor 104 may remove the specific pixels not corresponding to the first object OB1 from each of the sub-images 330b, so that only the specific image region corresponding to the first object OB1 is retained in each of the sub-images 330b. In short, the processor 104 may remove liver regions in which the tumor is not found from each of the sub-images 330b. However, the disclosure is not limited thereto.

In an embodiment, the second deep learning model may be realized by adopting the Unet model under the CNN framework or other similar models. However, the disclosure is not limited thereto. Besides, before being used to find the specific image region corresponding to the first object OB1, the second deep learning model may be firstly trained with training images in which specific regions of interest (ROIs) are labeled, so as to learn the features of the ROIs through the training images. Therefore, in the embodiment, in order for the second deep learning model to be capable of finding the specific image region corresponding to the first object OB1 (e.g., the image region of the tumor), the second deep learning model may firstly learn based on training sub-images in which tumors are set as the ROIs (the size of the training sub-image may correspond to the size of the sub-image 330b), so as to find the features of image regions having tumors. In an embodiment, the training sub-images may be obtained by evenly dividing up a liver training image in which the ROI (e.g., a tumor) is labeled, for example.

By dividing the liver training image into the training sub-images, the volume of data for the training of the second deep learning model may be increased, and the learning effect may thus be more favorable. Besides, since the size of each of the training sub-images is smaller, the parameters required for the second deep learning model during the training are also reduced. Accordingly, the training difficulty is reduced, and the accuracy of identification is increased.

In Step S260, the processor 104 may combine the sub-images 330b into a fourth CT image 340. In the embodiment, the processor 104 may combine the sub-images 330b into the fourth CT image 340 according to the distributed locations of the sub-images 330b (including only the specific image regions corresponding to the first object OB1) in the third CT image 330. In addition, the distributed location of each of the sub-images 330b in the third CT image 330 corresponds to the distributed location in the fourth CT image 340.

According to FIG. 3, since the sub-image 330b under consideration only includes the specific image region corresponding to the first object OB1, after the respective sub-images 330b are combined into the fourth CT image 340, the fourth CT image 340 only includes the first object OB1 (i.e., the tumor).

Then, in Step S270, the processor 104 may identify the object type of the first object OB1 based on the fourth CT image 340. In the embodiment, the processor 104 may input the fourth CT image 340 into the third deep learning model, so as to identify the object type of the first object OB1 (e.g., the tumor type of the tumor) according to the third deep learning model.

In an embodiment, the third deep learning model may be realized by adopting the NASnet model under the CNN framework or other similar models. However, the disclosure is not limited thereto. Besides, before the third deep learning model is used to find the object type of the first object OB1, the third deep learning model may be firstly trained with training images in which specific regions of interest (ROI) are labeled, so as to learn the features of the ROIs through the training images. Therefore, in the embodiment, in order for the third deep learning model to be capable of identifying the object type of the first object OB1 (e.g., the tumor type of the tumor), the third deep learning model may firstly learn based on tumor images corresponding one or more specific tumor types (e.g., hepatocellular carcinoma (HCC) tumors, hemangioma tumors, or focal nodular hyperplasia (FNH) tumors) as training images, so as to learn the corresponding features.

Based on the above, the image identifying method and the image identifying device according to the embodiments of the disclosure are capable of sequentially performing identification to find the first image region (e.g., the liver image region including the tumor), the specific image region corresponding to the first object (e.g., the tumor region located in the liver image region), and the object type of the first object (e.g., the tumor type of the tumor) according to different deep learning models after the pre-processing operations on the CT images. Accordingly, the performance and accuracy of identification can be more favorable.

Figure 4:
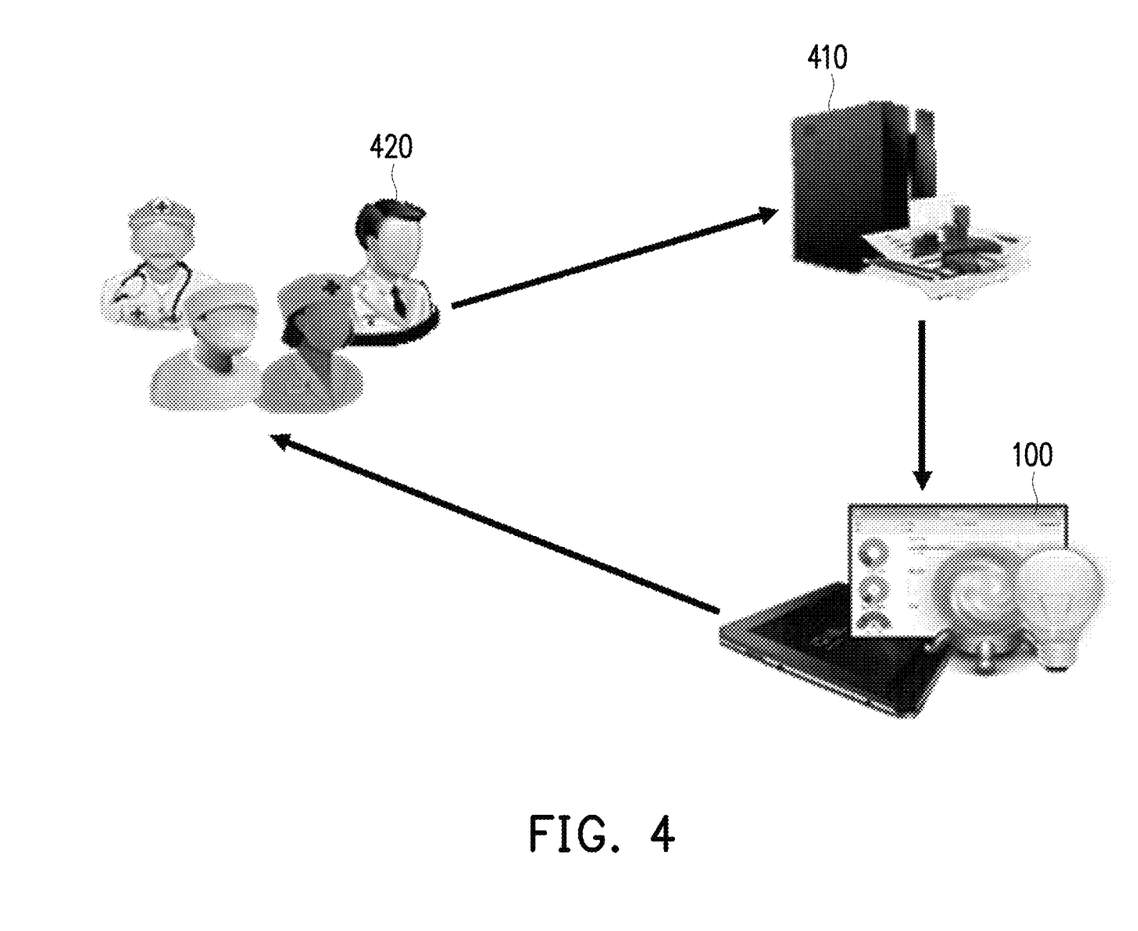
FIG. 4 is a view illustrating another usage scenario according to an embodiment of the disclosure.

Referring to FIG. 4, FIG. 4 is a view illustrating another usage scenario according to an embodiment of the disclosure. In the embodiment, a server 410 is a medical picture archiving and communication system (PACS), for example, and capable of storing various medical images such as the first CT image 310 shown in FIG. 3.

In an embodiment, when a doctor 420 intends to diagnose whether a patient has a specific disease (e.g., HCC, FNH, etc.) based on the first CT image 310, the doctor 420 may send a corresponding request to the server 410 through a client computer thereof. Then, in response to the request, the server 410 may transmit the first CT image 310 to the image identifying device 100, and the image identifying device 100 may perform relevant operations, such as pre-processing and identification, etc., on the first CT image 310 according to the teaching of the embodiments, so as to learn the object type (e.g., the tumor type) of the first object OB1 (e.g., the tumor). Then, the image identifying device 100 may return the original first CT image 310 and relevant identification results to the client computer for the doctor 420 to consider when making a diagnosis.

Besides, the image identifying device 100 may further overlay the first object OB1 as a semi-transparent image layer on the original first CT image 310, so that the doctor 420 may check the images more conveniently. However, the disclosure is not limited thereto.

In view of the foregoing, the image identifying method and the image identifying device according to the embodiments of the disclosure are capable of sequentially performing identification to find the first image region (e.g., the liver image region including the tumor), the specific image region corresponding to the first object (e.g., the tumor region located in the liver image region), and the object type of the first object (e.g., the tumor type of the tumor) according to different deep learning models after the pre-processing operations on the CT images (e.g., excluding the pixels whose channel values do not fall within the first range and performing the contrast enhancement algorithm). Accordingly, the performance and accuracy of identification can be more favorable.

In addition, the tumor identified through the embodiments of the disclosure may be further provided for relevant doctors to consider. Therefore, the disease diagnosis efficiency can be further facilitated.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. An image identifying method, comprising:
   retrieving a first computer tomographic (CT) image, wherein the first CT image comprises a plurality of first pixels, each of the first pixels has a channel value, and the channel value of each of the first pixels falls within a first range;
   retrieving a plurality of second pixels from the first pixels, and generating a second CT image based on the second pixels, wherein the channel value of each of the second pixels falls within a second range, and the second range is smaller than the first range;
   performing a contrast enhancement algorithm on the second CT image, so as to adjust a contrast of the second CT image;
   identifying a first image region in the second CT image to generate a third CT image, wherein the first image region comprises a first object;
   dividing the third CT image into a plurality of sub-images, and only reserving a specific image region corresponding to the first object in each of the sub-images;
   combining the sub-images into a fourth CT image; and
   identifying an object type of the first object based on the fourth CT image;
   wherein the channel value of each of the first pixels is a Hounsfield unit (HU) value, and the first range is between −2048 and 30000.

2. The image identifying method as claimed in claim 1, wherein the second range is between −70 and 200.

3. The image identifying method as claimed in claim 1, wherein the step of retrieving the second pixels from the first pixels and generating the second CT image based on the second pixels comprises:
   finding a plurality of third pixels from the first pixels, wherein the channel value of each of the third pixels falls outside the second range; and
   removing the third pixels from the first CT image to generate the second CT image only comprising the second pixels.

4. The image identifying method as claimed in claim 1, wherein the contrast enhancement algorithm is a histogram equalization algorithm.

5. The image identifying method as claimed in claim 1, wherein the step of identifying the first image region in the second CT image to generate the third CT image comprises:
   inputting the second CT image to a first deep learning model to find the first image region in the second CT image according to the first deep learning model; and
   removing the second pixels not belonging to the first image region from the second CT image to generate the third CT image.

6. The image identifying method as claimed in claim 5, wherein the step of only reserving the specific image region corresponding to the first object in each of the sub-images comprises:
   inputting a first sub-image of the sub-images to a second deep learning model to find the specific image region corresponding to the first object in the first sub-image according to the second deep learning model, wherein each of the sub-images comprises a plurality of specific pixels; and
   removing the specific pixels not belonging to the specific image region from the first sub-image, so that the first sub-image only comprises the specific image region corresponding to the first object.

7. The image identifying method as claimed in claim 5, wherein the step of dividing the third CT image into the sub-images comprises:
   evenly dividing the third CT image into the sub-images according to a predetermined size, and recording first distributed locations of the sub-images in the third CT image.

8. The image identifying method as claimed in claim 7, wherein the step of combining the sub-images into the fourth CT image comprises:

combining the sub-images into the fourth CT image according to the first distributed locations of the sub-images in the third CT image, wherein the first distributed location of each of the sub-images in the third CT image corresponds to a second distributed location in the fourth CT image.

9. The image identifying method as claimed in claim 6, wherein the step of identifying the object type of the first object based on the fourth CT image comprises:
inputting the fourth CT image to a third deep learning model, so as to identify the object type of the first object according to the third deep learning model.

10. The image identifying method as claimed in claim 1, wherein the first CT image is an abdominal CT image captured from an abdominal cavity.

11. The image identifying method as claimed in claim 10, wherein the first image region corresponds to a liver region in the abdominal cavity, and the first object is a tumor located in the liver region.

12. The image identifying method as claimed in claim 11, wherein the object type of the first object is a tumor type of the tumor.

13. An image identifying device, comprising:
a non-transitory storage circuit, storing a plurality of modules;
a processor, coupled to the non-transitory storage circuit and accessing the modules to perform the following steps:
retrieving a first computer tomographic (CT) image, wherein the first CT image comprises a plurality of first pixels, each of the first pixels has a channel value, and the channel value of each of the first pixels falls within a first range;
retrieving a plurality of second pixels from the first pixels, and generating a second CT image based on the second pixels, wherein the channel value of each of the second pixels falls within a second range, and the second range is smaller than the first range;
performing a contrast enhancement algorithm on the second CT image, so as to adjust a contrast of the second CT image;
identifying a first image region in the second CT image to generate a third CT image, wherein the first image region comprises a first object;
dividing the third CT image into a plurality of sub-images, and only reserving a specific image region corresponding to the first object in each of the sub-images;
combining the sub-images into a fourth CT image; and
identifying an object type of the first object based on the fourth CT image;
wherein the channel value of each of the first pixels is a Hounsfield unit (HU) value, and the first range is between −2048 and 30000.

14. The image identifying device as claimed in claim 13, wherein the second range is between −70 and 200.

15. The image identifying device as claimed in claim 13, wherein the processor is configured to:
find a plurality of third pixels from the first pixels, wherein the channel value of each of the third pixels falls outside the second range; and
remove the third pixels from the first CT image to generate the second CT image only comprising the second pixels.

16. The image identifying device as claimed in claim 13, wherein the contrast enhancement algorithm is a histogram equalization algorithm.

17. The image identifying device as claimed in claim 13, wherein the processor is configured to:
input the second CT image to a first deep learning model to find the first image region in the second CT image according to the first deep learning model; and
remove the second pixels not belonging to the first image region from the second CT image to generate the third CT image.

18. The image identifying device as claimed in claim 17, wherein the processor is configured to:
input a first sub-image of the sub-images to a second deep learning model to find the specific image region corresponding to the first object in the first sub-image according to the second deep learning model, wherein each of the sub-images comprises a plurality of specific pixels; and
remove the specific pixels not belonging to the specific image region from the first sub-image, so that the first sub-image only comprises the specific image region corresponding to the first object.

* * * * *